US012136145B2

(12) United States Patent
Tian et al.

(10) Patent No.: US 12,136,145 B2
(45) Date of Patent: Nov. 5, 2024

(54) SIGNAL AMPLITUDE FEATURE-BASED METHOD FOR FAST RECONSTRUCTING A MAGNETIC PARTICLE IMAGING AND DEVICE

(71) Applicant: INSTITUTE OF AUTOMATION, CHINESE ACADEMY OF SCIENCES, Beijing (CN)

(72) Inventors: Jie Tian, Beijing (CN); Peng Zhang, Beijing (CN); Hui Hui, Beijing (CN); Yimeng Li, Beijing (CN); Lin Yin, Beijing (CN); Xin Feng, Beijing (CN)

(73) Assignee: Institute Of Automation, Chinese Academy of Sciences, Beijing (CN)

( * ) Notice: Subject to any disclaimer, the term of this patent is extended or adjusted under 35 U.S.C. 154(b) by 367 days.

(21) Appl. No.: 17/811,738

(22) Filed: Jul. 11, 2022

(65) Prior Publication Data

US 2023/0027988 A1      Jan. 26, 2023

(30) Foreign Application Priority Data

Jul. 20, 2021   (CN) .......................... 202110816843.9

(51) Int. Cl.
   *G06T 11/00*        (2006.01)
   *A61B 5/00*         (2006.01)
   *A61B 5/0515*       (2021.01)

(52) U.S. Cl.
   CPC .......... *G06T 11/006* (2013.01); *A61B 5/0515* (2013.01); *A61B 5/7257* (2013.01)

(58) Field of Classification Search
   CPC ... G06T 11/006; G06T 11/003; A61B 5/0515; A61B 5/7257; A61B 5/0033; G01R 33/0094; G01R 33/1276
   See application file for complete search history.

(56) References Cited

U.S. PATENT DOCUMENTS

2013/0290223 A1* 10/2013 Chapelle ................. G06N 20/00
                                                              706/12
2018/0350111 A1* 12/2018 Chae ...................... G06T 11/006

* cited by examiner

*Primary Examiner* — Christopher M Brandt
(74) *Attorney, Agent, or Firm* — Schwegman Lundberg & Woessner, P.A.

(57) ABSTRACT

The present disclosure includes: transforming a time-domain voltage signal collected by an MPI system device to a frequency domain; calculating a square root of a square sum of a real part and an imaginary part at each frequency point of a frequency domain signal; arranging acquired amplitudes in a descending order, and acquiring a screening threshold by an amplitude ratio method; screening an amplitude through the screening threshold and constructing frequency domain signal data; acquiring a row vector of a system matrix corresponding to each frequency point of the data, so as to construct an update system matrix; and solving, based on the frequency domain signal array and the update system matrix, an inverse problem in a form of a least square based on an L2 constraint to obtain a three-dimensional magnetic particle concentration distribution result, so as to achieve a fast reconstruction of the MPI system.

8 Claims, 3 Drawing Sheets

SIGNAL AMPLITUDE FEATURE-BASED METHOD FOR FAST RECONSTRUCTING A MAGNETIC PARTICLE IMAGING AND DEVICE

CROSS-REFERENCE TO RELATED APPLICATION

This application claims the priority of Chinese Patent Application No. 202110816843.9 filed on Jul. 20, 2021 in the China National Intellectual Property Administration, the content of which is incorporated herein by reference in entirety.

TECHNICAL FIELD

The present disclosure relates to a field of a stereo reconstruction technology in a three-dimensional magnetic particle imaging system without a magnetic field point, and in particularly, to a signal amplitude feature-based method for fast reconstructing a magnetic particle imaging and a device.

BACKGROUND

In a clinical diagnosis and detection, how to accurately and objectively locate a tumor and other lesions has been an international research hotspot and a challenging problem. Existing medical imaging technologies such as CT, MRI, SPECT and the like have problems of great harm, poor positioning, low precision and the like. However, in recent years, a completely new tracer-based imaging method—Magnetic Particle Imaging (MPI) technology, has been proposed. The MPI may accurately locate a tumor or a target by detecting a spatial concentration distribution of superparamagnetic iron oxide nanoparticles (SPIONs) harmless to a human body, and it is a three-dimensional high-spatial-temporal resolution and high-sensitivity imaging which is not limited by an imaging depth. In addition, the MPI does not display an anatomical structure and has no interference of a background signal, so that a strength of a signal is directly related to a concentration of a tracer. Therefore, the MPI is a new method with a great potential for a medical application.

A reconstruction method of today's MPI system may be basically divided into two categories: a system matrix method and an X-space method. A great number of studies have showed that, compared with a system matrix reconstruction method, the X-space method has a higher reconstruction speed, but has a difficulty in improving a resolution of a reconstructed image. Therefore, the system matrix method is always a main research direction of an image reconstruction. At present, researchers have achieved a dynamic three-dimensional magnetic particle imaging technology based on the system matrix method through a supercomputing platform. However, only a dynamic reconstruction at a level of several frames may be achieved due to a large amount of reconstruction calculation and a low frame rate of a dynamic image. At the same time, due to a presence of a huge data transmission and matrix operation in a calculation process, the technology depends heavily on a hardware device, which puts forward strict requirements on various devices for storage, transmission, calculation and the like.

SUMMARY

In order to solve the above-mentioned problem in the prior art, that is, the problem of a low stereo reconstruction efficiency and a high requirement for device resources in a three-dimensional magnetic particle imaging system caused by a huge data volume and calculated amount, the present disclosure provides a signal amplitude feature-based method for fast reconstructing a magnetic particle imaging, including:

transforming a time-domain voltage signal collected by an MPI system device to a frequency domain, so as to obtain a frequency domain complex voltage signal u;

respectively calculating a square root of a square sum of a real part and an imaginary part at each frequency point of the frequency domain complex voltage signal u, so as to obtain an amplitude at the each frequency point;

arranging the amplitude at the each frequency point in a descending order so as to obtain an amplitude matrix D, and acquiring a screening threshold $i_0$ by an amplitude ratio method;

screening an element of the amplitude matrix D based on the screening threshold $i_0$, and constructing a frequency domain signal array $u_0$ based on the screened elements $D_{1 \sim i_0}$;

selecting row vectors $a_{1 \sim i_0}$ of a system matrix A corresponding to each frequency point of the frequency domain signal array $u_0$, so as to construct an update system matrix $A_0$; and solving, based on the frequency domain signal array $u_0$ and the update system matrix $A_0$, an inverse problem in a form of a least square based on an L2 constraint by an convex optimization method to obtain a three-dimensional magnetic particle concentration distribution result, so as to achieve a fast reconstruction of the MPI system.

In some embodiments, the acquiring a screening threshold $i_0$ by an amplitude ratio method includes:

calculating a sum N of all amplitudes of the amplitude matrix D, and dividing a sum of amplitudes sorted in a descending order of 1-th to i-th by N as a value of an amplitude proportion element $M_i$; and selecting a value i corresponding to m elements in the amplitude ratio element $M_i$ to be recorded as a screening threshold $i_0$, wherein a difference value between the value i and a set first threshold is smaller than a set second threshold.

In some embodiments, the set first threshold is 0.8.
In some embodiments, the amplitude proportion element $M_i$ is expressed as:

$$M_i = \Sigma_{k=1}^{i} D_k / N$$

wherein $D_k$ represents a k-th amplitude in the amplitude matrix D, N represents the sum of all amplitudes in the amplitude matrix D, and i represents an i-th amplitude of the amplitudes sorted in the descending order of 1-th to i-th.

In some embodiments, the convex optimization method is one of a Kaczmarz method, an ADMM method and a TV-L2 method.

In another aspect of the present disclosure, a signal amplitude feature-based system for performing an MPI fast reconstruction is provided, including:

a signal transforming module configured to transform a time-domain voltage signal collected by an MPI system device to a frequency domain, so as to obtain a frequency domain complex voltage signal u;

an amplitude calculating module configured to respectively calculate a square root of a square sum of a real part and an imaginary part at each frequency point of the frequency domain complex voltage signal u, so as to obtain an amplitude at the each frequency point;

a screening threshold acquiring module configured to arrange the amplitude at the each frequency point in a descending order so as to obtain an amplitude matrix D, and acquiring a screening threshold $i_0$ by an amplitude ratio method;

an amplitude screening module configured to screen an element of the amplitude matrix D based on the screening threshold $i_0$, and constructing a frequency domain signal array $u_0$ based on the screened elements $D_{1\sim i_0}$;

a system matrix updating module configured to select row vectors $a_{1\sim i_0}$ of a system matrix A corresponding to each frequency point of the frequency domain signal array $u_0$, so as to construct an update system matrix $A_0$; and a reconstructing module configured to solving, based on the frequency domain signal array $u_0$ and the update system matrix $A_0$, an inverse problem in a form of a least square based on an L2 constraint by an convex optimization method to obtain a three-dimensional magnetic particle concentration distribution result, so as to achieve a fast reconstruction of the MPI system.

In a third aspect of the present disclosure, an electronic device is provided, including:

at least one processor; and a memory in communication with the at least one processor;

wherein the memory has an instruction executable by the processor stored therein, and the instruction is configured to be executed by the processor so as to implement the above-mentioned signal amplitude feature-based method for fast reconstructing a magnetic particle imaging.

In a fourth aspect of the present disclosure, there is provided a computer-readable storage medium, and the computer-readable storage medium has a computer instruction stored therein, and the computer instruction is configured to be executed by the computer so as to implement the above-mentioned signal amplitude feature-based method for fast reconstructing a magnetic particle imaging.

BRIEF DESCRIPTION OF THE DRAWINGS

The other features, objects and advantages of the present disclosure will be clearer by reading the detailed description of non-limiting embodiments made with reference to the following accompanying drawings.

DETAILED DESCRIPTION OF EMBODIMENTS

Figure 1:
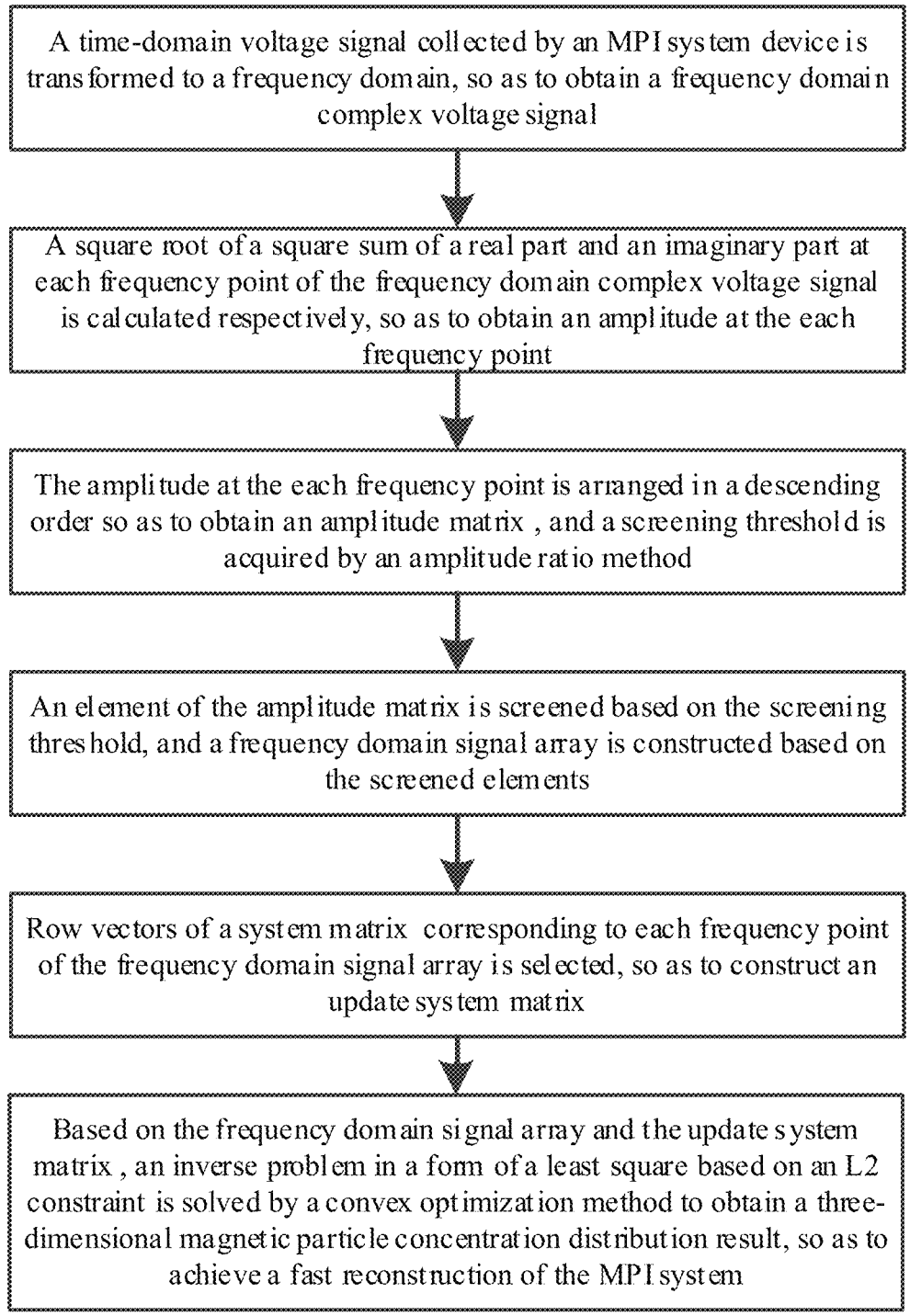
FIG. 1 shows a schematic flow diagram of a signal amplitude feature-based method for fast reconstructing a magnetic particle imaging according to the present disclosure.

The present disclosure will be further described in detail below with reference to the accompanying drawings and examples. It will be appreciated that the specific embodiments described herein are merely illustrative of the present disclosure and are not intended to limit the scope of the present disclosure. In addition, it should be noted that, for convenience of description, only portions related to the present disclosure are illustrated in the accompanying drawings.

It should be noted that, embodiments and features of the embodiments in the present disclosure may be combined with each other without a conflict. The present disclosure will be described in detail below with reference to the accompanying drawings in conjunction with the embodiments.

The present disclosure provides a signal amplitude feature-based method for fast reconstructing a magnetic particle imaging. The method may screen an original signal by a method of amplitude ratio and threshold calculation, so that the signal may maintain the same information content and distribution characteristics as those of the original signal with a small amount of data. At the same time, a size of a system matrix required for the reconstruction may be reduced together by a frequency domain signal-based system matrix screening, so that the calculated amount in a reconstruction process may be greatly reduced (less than 1% of an original data amount), which may greatly improve the reconstruction speed and reduce a required hardware device requirement.

In the present disclosure, there is provided a signal amplitude feature-based method for fast reconstructing a magnetic particle imaging, including:

step S10 of transforming a time-domain voltage signal collected by an MPI system device to a frequency domain, so as to obtain a frequency domain complex voltage signal u;

step S20 of respectively calculating a square root of a square sum of a real part and an imaginary part at each frequency point of the frequency domain complex voltage signal u, so as to obtain an amplitude at the each frequency point;

step S30 of arranging the amplitude at the each frequency point in a descending order so as to obtain an amplitude matrix D, and acquiring a screening threshold $i_0$ by an amplitude ratio method;

step S40 of screening an element of the amplitude matrix D based on the screening threshold $i_0$, and constructing a frequency domain signal array $u_0$ based on the screened elements $D_{1\sim i_0}$;

step S50 of selecting row vectors $a_{1\sim i_0}$ of a system matrix A corresponding to each frequency point of the frequency domain signal array $u_0$, so as to construct an update system matrix $A_0$; and step S60 of solving, based on the frequency domain signal array $u_0$ and the update system matrix $A_0$, an inverse problem in a form of a least square based on an L2 constraint by an convex optimization method to obtain a three-dimensional magnetic particle concentration distribution result, so as to achieve a fast reconstruction of the MPI system.

In order to more clearly describe the signal amplitude feature-based method for fast reconstructing a magnetic particle imaging in the present disclosure, the steps in the embodiments of the present disclosure will be described below in detail with reference to FIG. 1.

In a first embodiment of the present disclosure, the signal amplitude feature-based method for fast reconstructing a magnetic particle imaging includes step S10 to step S60. The steps are described in detail as follows:

In step S10, a time-domain voltage signal collected by an MPI system device is transformed to a frequency domain, so as to obtain a frequency domain complex voltage signal u.

In an embodiment of the present disclosure, the time-domain voltage signal collected by the MPI system device is transformed to a frequency domain through a Fourier transform, so as to obtain the frequency domain complex voltage signal u in a complex form.

In step S20, a square root of a square sum of a real part and an imaginary part at each frequency point of the frequency domain complex voltage signal u is calculated respectively, so as to obtain an amplitude of the each frequency point.

In step S30, the amplitude at the each frequency point is arranged in a descending order so as to obtain an amplitude matrix D, and a screening threshold $i_0$ is acquired by an amplitude ratio method.

In step S31, a sum N of all amplitudes of the amplitude matrix D is calculated, and a sum of amplitudes sorted in a descending order of 1-th to i-th is divided by N as a value of an amplitude proportion element $M_i$.

The amplitude proportion element $M_i$ is expressed as equation (1).

$$M_i = \sum_{k=1}^{i} D_k/N \quad (1)$$

$D_k$ represents a k-th amplitude in the amplitude matrix D, N represents the sum of all amplitudes in the amplitude matrix D, and i represents an i-th amplitude of the amplitudes sorted in a descending order of 1-th to i-th.

In step S32, a value i corresponding to m elements in the amplitude ratio element $M_i$ is selected to be recorded as a screening threshold $i_0$, and a difference value between the value i and a set first threshold is smaller than a set second threshold.

In an embodiment of the present disclosure, the set first threshold is 0.8, and a value i corresponding to m elements closest to 0.8 is acquired to be recorded as the screening threshold $i_0$.

Figure 2:
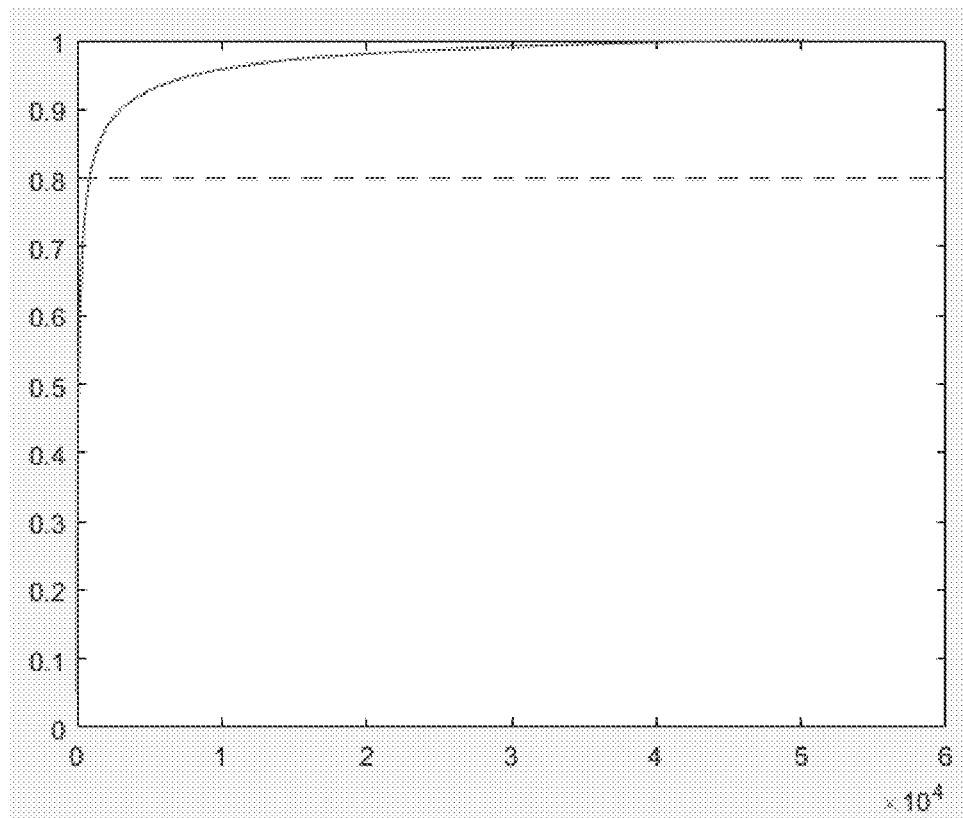
FIG. 2 shows an amplitude proportion diagram and a segmentation threshold of a signal amplitude feature-based method for fast reconstructing a magnetic particle imaging according to an embodiment of the present disclosure.

FIG. 2 shows an amplitude proportion diagram and a segmentation threshold of a signal amplitude feature-based method for fast reconstructing a magnetic particle imaging according to an embodiment of the present disclosure, where an abscissa represents a position k of an amplitude matrix arranged according to a descending order of amplitudes, an ordinate represents an amplitude ratio M, a curve represents a change in the amplitude ratio as the number of contained amplitudes increases, and a dashed line represents a threshold value.

In step S40, an element of the amplitude matrix D is screened based on the screening threshold $i_0$, and a frequency domain signal array $u_0$ is constructed based on the screened elements $D_{1-i_0}$.

Figure 3:
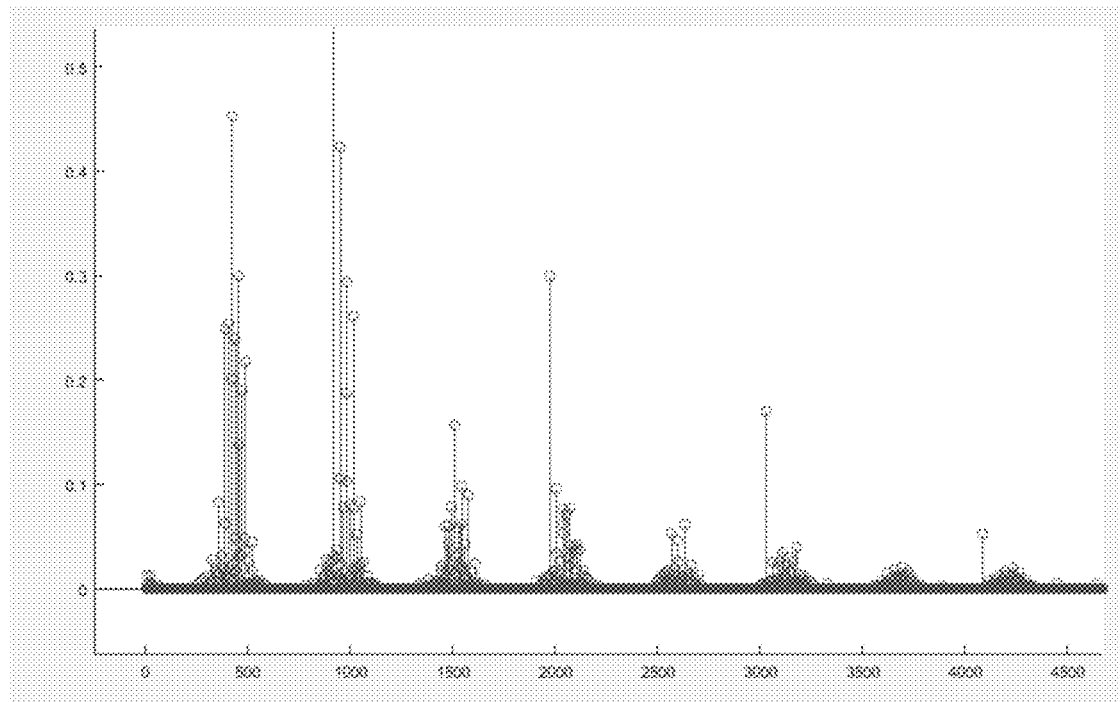
FIG. 3 shows a stem-and-leaf diagram of a screened signal distribution of a signal amplitude feature-based method for fast reconstructing a magnetic particle imaging according to an embodiment of the present disclosure.

FIG. 3 shows a stem-and-leaf diagram of a screened signal distribution of a signal amplitude feature-based method for fast reconstructing a magnetic particle imaging according to an embodiment of the present disclosure, where an abscissa represents a frequency point value, an ordinate represents a normalized amplitude value, and each hollow circle represents an amplitude value at the frequency point. FIG. 3 shows a stem-and-leaf diagram of a signal distribution of first 625 larger amplitude values screened, in which it is indicated that the amplitude values are concentrated around a main frequency point.

In step S50, row vectors $a_{1-i_0}$ of a system matrix A corresponding to each frequency point of the frequency domain signal array $u_0$ is selected, so as to construct an update system matrix $A_0$.

A small measurement sample with a standard concentration may be used to move and traverse an entire FOV, and a signal is measured once after each movement as a row of the matrix, so that an entire system matrix A may be acquired after the traverse. The system matrix A may be acquired by other methods, which is not described in detail in the present disclosure.

In step S60, based on the frequency domain signal array $u_0$ and the update system matrix $A_0$, an inverse problem in a form of a least square based on an L2 constraint is solved by a convex optimization method to obtain a three-dimensional magnetic particle concentration distribution result, so as to achieve a fast reconstruction of the MPI system.

The convex optimization method is one of a Kaczmarz method, an ADMM method and a TV-L2 method. In an embodiment of the present disclosure, the Kaczmarz method may be used.

Figure 4:
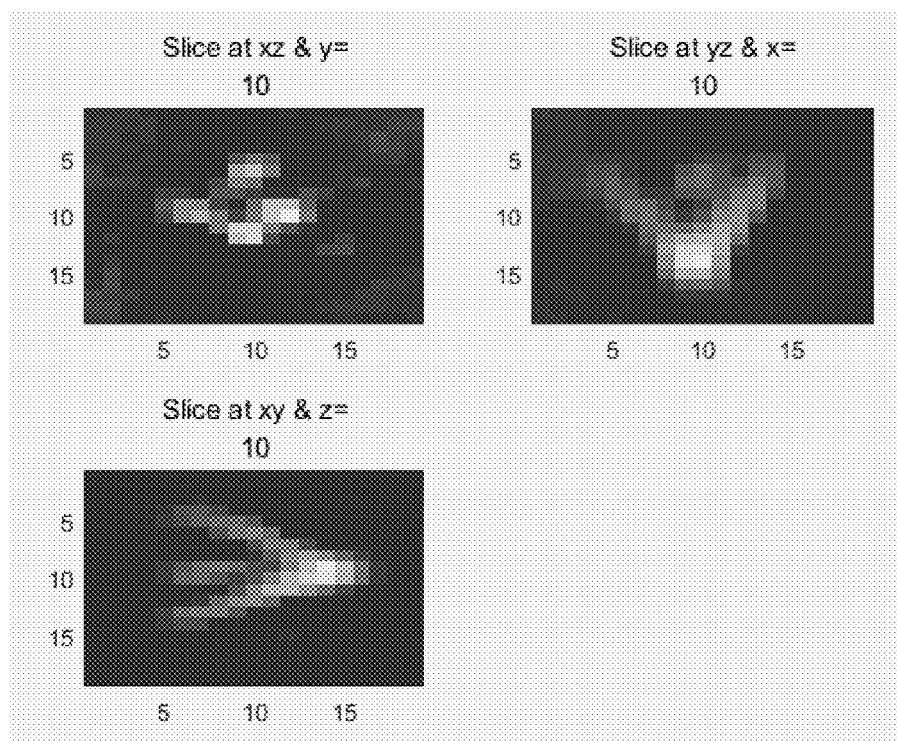
FIG. 4 shows a three-dimensional slice diagram of a reconstruction result of a signal amplitude feature-based method for fast reconstructing a magnetic particle imaging according to an embodiment of the present disclosure.

FIG. 4 shows a three-dimensional slice diagram of a reconstruction result of a signal amplitude feature-based method for fast reconstructing a magnetic particle imaging according to an embodiment of the present disclosure, where an abscissa is an x-axis coordinate of a location, an ordinate is a y-axis coordinate of the location, and Slice at xz & y=10 represents that a corresponding view is a slice of an xy plane at y=10. Upper left, upper right and lower left views in FIG. 4 represent slices at different angles.

Although the above-mentioned embodiments have described the steps in the above-mentioned sequence, those skilled in the art will appreciate that, in order to achieve the effect of the present embodiment, different steps are not necessarily performed in such a sequence, and may be performed simultaneously (in parallel) or in an inverse sequence, and these simple variations are within the scope of the present disclosure.

In a second embodiment of the present disclosure, there is provided a signal amplitude feature-based system for performing an MPI fast reconstruction, including:

a signal transforming module configured to transform a time-domain voltage signal collected by an MPI system device to a frequency domain, so as to obtain a frequency domain complex voltage signal u;

an amplitude calculating module configured to respectively calculate a square root of a square sum of a real part and an imaginary part at each frequency point of the frequency domain complex voltage signal u, so as to obtain an amplitude at the each frequency point;

a screening threshold acquiring module configured to arrange the amplitude at the each frequency point in a descending order so as to obtain an amplitude matrix D, and acquiring a screening threshold $i_0$ by an amplitude ratio method;

an amplitude screening module configured to screen an element of the amplitude matrix D based on the screening threshold $i_0$, and constructing a frequency domain signal array $u_0$ based on the screened elements $D_{1-i_0}$;

a system matrix updating module configured to select row vectors $a_{1-i_0}$ of a system matrix A corresponding to each frequency point of the frequency domain signal array $u_0$, so as to construct an update system matrix $A_0$; and a reconstructing module configured to solving, based on the frequency domain signal array $u_0$ and the update system matrix $A_0$, an inverse problem in a form of a least square based on an L2 constraint by an convex optimization method to obtain a three-dimensional magnetic particle concentration distribution result, so as to achieve a fast reconstruction of the MPI system.

Those skilled in the art will clearly understand that, for convenience and simplicity of description, the specific working process and related description of the above-mentioned system may be explained with reference to the corresponding process in the method embodiment described above, which will not repeated here.

It should be noted that the signal amplitude feature-based system for performing an MPI fast reconstruction provided in the above-mentioned embodiments is only illustrated by a division of the above-mentioned functional modules. In practical applications, an allocation of the above-mentioned functions may be completed by different functional modules as needed, that is, the modules or steps in the embodiments of the present disclosure are further decomposed or combined. For example, the modules in the above-mentioned embodiments may be combined into a module, or may be further split into a plurality of sub-modules, so as to complete all or part of the functions described above. Names of the modules and steps involved in the embodiments of the present disclosure are only to distinguish each modules or step, and are not to be regarded as an improper limitation on the present disclosure.

In a third embodiment of the present disclosure, there is provided an electronic device including:
at least one processor; and
a memory in communication with the at least one processor;
wherein the memory has an instruction executable by the processor stored therein, and the instruction is configured to be executed by the processor so as to implement the above-mentioned signal amplitude feature-based method for fast reconstructing a magnetic particle imaging.

In a fourth embodiment of the present disclosure, there is provided a computer-readable storage medium, and the computer-readable storage medium has a computer instruction stored therein, and the computer instruction is configured to be executed by the computer so as to implement the above-mentioned signal amplitude feature-based method for fast reconstructing a magnetic particle imaging.

Beneficial Effects of the Present Disclosure:
(1) The signal amplitude feature-based method for fast reconstructing a magnetic particle imaging in the present disclosure may greatly reduce a calculated amount required by a reconstruction without reducing a reconstruction precision, and may further improve a reconstruction speed and reduce a requirement for a reconstruction hardware, and may be used to improve a frame rate of a three-dimensional dynamic MPI imaging.

(2) The signal amplitude feature-based method for fast reconstructing a magnetic particle imaging in the present disclosure may separate the reconstruction from the supercomputing platform due to a significant reduction in a calculated amount, and may complete the reconstruction by only a common workstation, which may improve a popularization potential of an MPI device.

Those skilled in the art will clearly understand that, for convenience and simplicity of description, the specific working process and related descriptions of the storage device and the processing device described above may be explained with reference to the corresponding process in the method embodiment described above, which will not repeated here.

Those skilled in the art will appreciate that modules and method steps of each example described in conjunction with the embodiments disclosed herein may be implemented by an electronic hardware, a computer software, or a combinations thereof. Programs corresponding to software modules and method steps may be placed in a random access memory (RAM), a memory, a read only memory (ROM), an electrically programmable ROM, an electrically erasable programmable ROM, a register, a hard disk, a removable disk, a CD-ROM, or any other form of storage medium known in the art. In order to clearly illustrate an interchangeability between an electronic hardware and an electronic software, components and steps of each example have been generally described above in terms of their functionality. Whether these functions are performed by the electronic hardware or the electronic software depends on a particular application and design constraint of the technical solution. Those skilled in the art may implement the described function using different methods for each particular application, but such an implementation should not be considered beyond the scope of the present disclosure.

The terms such as "first," "second," and the like are used to distinguish between similar elements and not necessarily to describe or imply a particular order or sequence.

The term "including," or any other similar expression, is intended to cover a non-exclusive inclusion, so that a process, a method, an article or a device/apparatus including a list of elements include not only those elements, but also other elements not expressly listed, or elements inherent to the process, the method, the article or the device/apparatus.

So far, the technical solution of the present disclosure has been described in conjunction with the embodiments shown in the accompanying drawings. However, those skilled in the art will easily appreciate that the scope of protection of the present disclosure is obviously not limited to these specific embodiments. Without departing from the principle of the present disclosure, those skilled in the art may make equivalent changes or substitutions of related technical features, and these technical solutions to be changed or substituted should all fall within the scope of protection of the present disclosure.

What is claimed is:
1. A signal amplitude feature-based method for fast reconstructing a magnetic particle imaging, comprising:
transforming a time-domain voltage signal collected by an MPI system device to a frequency domain, so as to obtain a frequency domain complex voltage signal u;
respectively calculating a square root of a square sum of a real part and an imaginary part at each frequency point of the frequency domain complex voltage signal u, so as to obtain an amplitude at the each frequency point;
arranging the amplitude at the each frequency point in a descending order so as to obtain an amplitude matrix D, and acquiring a screening threshold $i_0$ by an amplitude ratio method;
screening an element of the amplitude matrix D based on the screening threshold $i_0$, and constructing a frequency domain signal array $u_0$ based on the screened elements $D_{1 \sim i_0}$;
selecting row vectors $a_{1 \sim i_0}$ of a system matrix A corresponding to each frequency point of the frequency domain signal array $u_0$, so as to construct an update system matrix $A_0$; and solving, based on the frequency domain signal array $u_0$ and the update system matrix $A_0$, an inverse problem in a form of a least square based on an L2 constraint by an convex optimization method to obtain a three-dimensional magnetic particle concentration distribution result, so as to achieve a fast reconstruction of the MPI system.

2. The method according to claim 1, wherein the acquiring a screening threshold $i_0$ by an amplitude ratio method comprises:

calculating a sum N of all amplitudes of the amplitude matrix D, and dividing a sum of amplitudes sorted in a descending order of 1-th to i-th by N as a value of an amplitude proportion element $M_i$; and selecting a value i corresponding to m elements in the amplitude ratio element $M_i$ to be recorded as a screening threshold $i_0$, wherein a difference value between the value i and a set first threshold is smaller than a set second threshold.

3. The method according to claim 2, wherein the set first threshold is 0.8.

4. The method according to claim 2, wherein the amplitude proportion element $M_i$ is expressed as:

$$M_i = \sum_{k=1}^{i} D_k / N$$

wherein $D_k$ represents a k-th amplitude in the amplitude matrix D, N represents the sum of all amplitudes in the amplitude matrix D, and i represents an i-th amplitude of the amplitudes sorted in the descending order of 1-th to i-th.

5. The method according to claim 1, wherein the convex optimization method is one of a Kaczmarz method, an ADMM method and a TV-L2 method.

6. A signal amplitude feature-based system for performing an MPI fast reconstruction, comprising:

a signal transforming module configured to transform a time-domain voltage signal collected by an MPI system device to a frequency domain, so as to obtain a frequency domain complex voltage signal u;

an amplitude calculating module configured to respectively calculate a square root of a square sum of a real part and an imaginary part at each frequency point of the frequency domain complex voltage signal u, so as to obtain an amplitude at the each frequency point;

a screening threshold acquiring module configured to arrange the amplitude at the each frequency point in a descending order so as to obtain an amplitude matrix D, and acquiring a screening threshold $i_0$ by an amplitude ratio method;

an amplitude screening module configured to screen an element of the amplitude matrix D based on the screening threshold $i_0$, and constructing a frequency domain signal array $u_0$ based on the screened elements $D_{1 \sim i_0}$;

a system matrix updating module configured to select row vectors $a_{1 \sim i_0}$ of a system matrix A corresponding to each frequency point of the frequency domain signal array $u_0$, so as to construct an update system matrix $A_0$; and a reconstructing module configured to solving, based on the frequency domain signal array $u_0$ and the update system matrix $A_0$, an inverse problem in a form of a least square based on an L2 constraint by an convex optimization method to obtain a three-dimensional magnetic particle concentration distribution result, so as to achieve a fast reconstruction of the MPI system.

7. An electronic device, comprising:

at least one processor; and a memory in communication with the at least one processor;

wherein the memory has an instruction executable by the processor stored therein, and the instruction is configured to be executed by the processor so as to implement the signal amplitude feature-based method for fast reconstructing a magnetic particle imaging according to claim 1.

8. A non-transitory computer-readable storage medium, wherein the computer-readable storage medium has a computer instruction stored therein, and the computer instruction is configured to be executed by the computer so as to implement the signal amplitude feature-based method for fast reconstructing a magnetic particle imaging according to claim 1.

* * * * *